United States Patent [19]

Cahn et al.

[11] 4,048,251

[45] Sept. 13, 1977

[54] AUTOREFRIGERATED ISOMERIZATION PROCESS

[75] Inventors: Robert P. Cahn, Millburn; Michael Siskin, Maplewood, both of N.J.

[73] Assignee: Exxon Research and Engineering Company, Linden, N.J.

[21] Appl. No.: 646,285

[22] Filed: Jan. 2, 1976

[51] Int. Cl.² .............................................. C07C 5/28
[52] U.S. Cl. ........................... 260/683.68; 260/683.75
[58] Field of Search ...................... 260/683.75, 683.65, 260/683.7, 666 P, 683.4 F, 683.68

[56] References Cited

U.S. PATENT DOCUMENTS

| | | | |
|---|---|---|---|
| 2,232,674 | 2/1941 | Pyzel | 260/683.4 F |
| 2,418,146 | 4/1947 | Upham | 260/683.4 F |

*Primary Examiner*—George Crasanakis
*Attorney, Agent, or Firm*—John W. Ditsler

[57] ABSTRACT

Acyclic and alicyclic aliphatic hydrocarbons are isomerized to form a product of enhanced octane by contacting same, in a reaction zone and in the presence of hydrogen, with a catalyst comprising a difficultly reducible metal halide in combination with at least a molar equivalent of hydrogen halide, said reaction zone comprising at least one temperature zone, the temperature in at least one zone being controlled by using said hydrogen halide as an autorefrigerant. In a preferred embodiment, at least a portion of the autorefrigerant evolved from the reaction zone is condensed and used to extract at least a portion of the metal halide component of the catalyst from at least a portion of the hydrocarbon product. A preferred catalyst is tantalum pentafluoride, niobium pentafluoride or their mixtures in combination with at least a five-fold molar excess of hydrogen fluoride.

26 Claims, 1 Drawing Figure

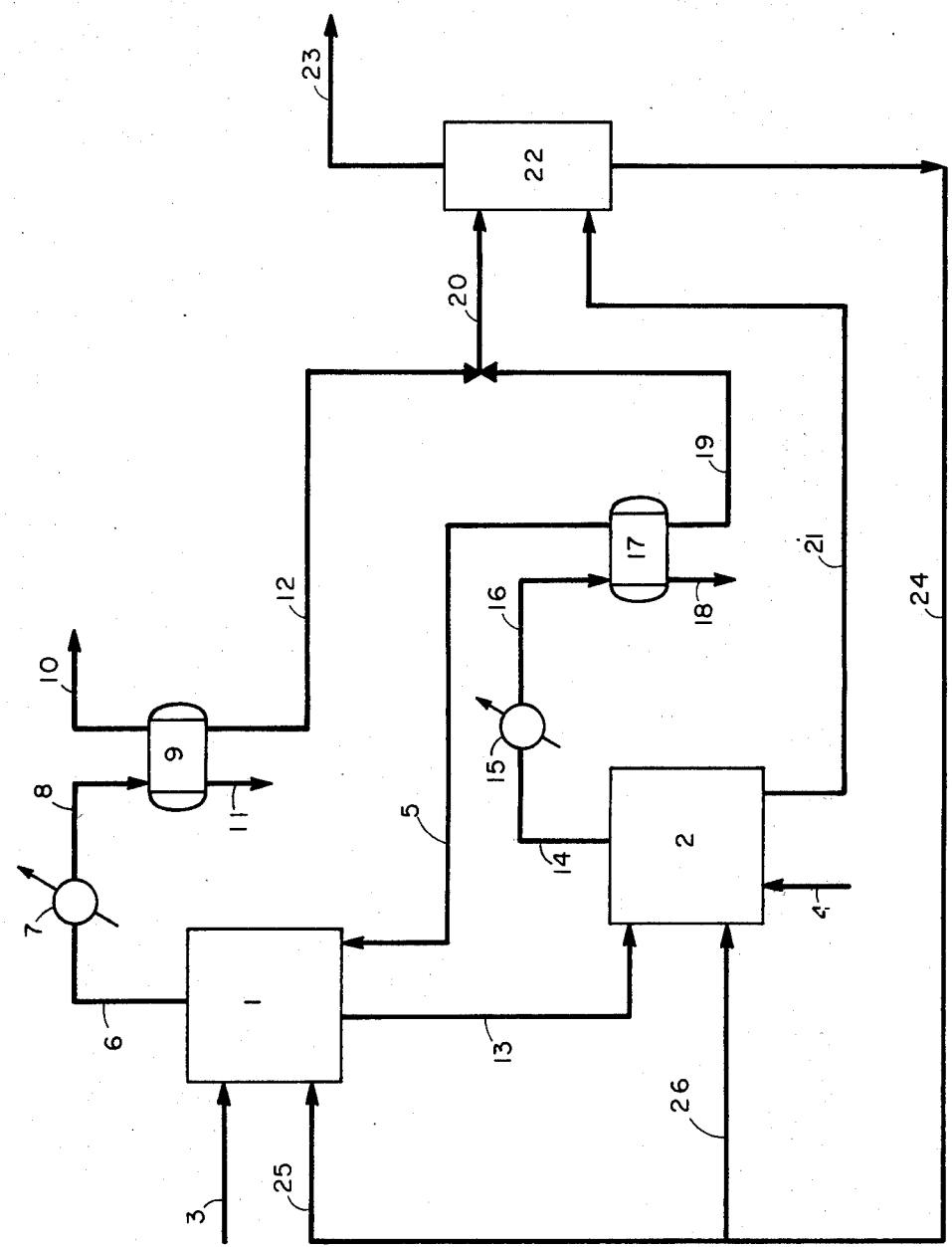

AUTOREFRIGERATED ISOMERIZATION PROCESS

BACKGROUND OF THE INVENTION

1. Field of the Invention

The present invention relates to a process for the conversion of hydrocarbon feed stocks. More particularly, this invention relates to a catalytic process for the hydroisomerization of saturated acyclic and alicyclic hydrocarbons in a reaction zone comprising at least one temperature zone, the temperature in at least one zone being controlled by autorefrigeration.

2. Description of the Prior Art

Hydrocarbon conversion processes involving the use of metal halide based catalysts have been extensively described in the prior art. For example, U.S. Pat. Nos. 2,683,763 and 2,683,764 disclose that tantalum pentalfuoride or columbium (niobium) pentafluoride in combination with hydrogen fluoride can be used to refine hydrocarbon oils or to promote the disproportionation of alkyl-substituted aromatic materials. The patents also teach that hydrogen fluoride/tantalum pentafluoride and hydrogen fluoride/columbium pentafluoride are powerful catalysts for isomerization, alkylation, cracking and other reactions of aromatics. U.S. Pat. No. 3,201,494, teaches that niobium pentafluoride or tantalum pentafluoride in combination with hydrofluoric acid can be employed for the isomerization or purified hexane feed stocks. More recently, application No. 445,163, filed Feb. 25, 1974, which issued as U.S. Pat. No. 3,948,761 discloses a process for hydroiosomerizing saturated alicyclic and acyclic hydrocarbons in the presence of a catalysts comprising a difficultly reducible metal halide in combination with at least a molar equivalent of hydrogen halide. The isomerization of hydrocarbons using more than one temperature zone to form an isomerate of enhanced octane is also known in the art (see for example U.S. Pat Nos. 3,054,832 and 3,201,494). In addition, it is known that it is necessary to remove the heat evolved during isomerization to maintain the reaction temperature at a desired level. This may be accomplished by interstage cooling using water or a refrigerant, pump-around cooling and the like (see for example U.S. Pat. No. 3,541,181).

However, none of the foregoing prior art teaches a hydroisomerization process having one or more temperature zones wherein the temperature in at least one zone is controlled by autorefrigeration, thereby eliminating the need for indirect heat exchange to remove the exothermic heat of reaction and to form an isomerate of enhanced octane.

SUMMARY OF THE INVENTION

Now according to the present invention, it has been discovered that saturated alicyclic and acyclic hydrocarbons may be hydroisomerized to form a product of enhanced octane in the presence of a catalyst comprising a difficulty reducible metal halide, preferably a metal fluoride, in combination with at least a molar equivalent, preferably a molar excess, of hydrogen halide, wherein said hydroisomerization occurs in one or more reaction zones, each reaction zone comprising at least one temperature zone with the temperature in at least one zone being controlled by autorefrigeration. In one embodiment of the present invention, the hydrocarbons are hydroisomerized in a single temperature zone. In another embodiment of the present invention, said hydrocarbons are hydroisomerized first at a relatively high temperature to accelerate the rate of reaction and then at a lower temperature to shift the thermodynamic equilibrium toward increased yields of branched paraffinic isomers which have a higher motor octane number (MON). In each embodiment, the exothermic heat of reaction associated with the isomerization reaction is removed by allowing the hydrogen halide to boil off, i.e. autorefrigeration, thereby avoiding the need for indirect heat exchange. In a preferred embodiment, at least a portion of the hydrogen halide boiled off is condensed and, before being returned to the reaction zone, is used to extract at least a portion of the metal halide present in the hydrocarbon product discharged from the isomerization reaction zone.

In general, temperatures at which isomerization is conducted are not critical to the practice of the present invention and may range from about 0° C. to about the critical temperature of the protonic acid, i.e. the hydrogen halide. However, temperatures are important to the autorefrigeration as will be discussed hereinafter. The only limitation in pressure is that the hydrogen partial pressure be sufficient to maintain acceptable catalyst activity, and that the total pressure be sufficient to maintain at least a portion of the catalyst and the hydrocarbon feedstock in the liquid phase.

BRIEF DESCRIPTION OF THE DRAWING

The single FIGURE is a diagrammatic representation of one embodiment of the present invention.

DETAILED DESCRIPTION OF THE INVENTION

The hydroisomerization process employed in thepresent invention is that described in US. Pat. No. 3,948,761, the disclosures of which are incorporated herein by reference, which relates to converting acyclic and alicyclic aliphatic hydrocarbons having at least four carbon atoms to a product having a enhanced octane. Typically, acyclic hydrocarbons having at least four carbon atoms, that is, straight chain or branched chain paraffins having from about 4 to 10 carbon atoms, preferably about 4 to 8 carbon atoms, are converted to branched hydrocarbons having higher octane ratings. Additionally, alicyclic hydrocarbons (naphthaenes) having at least about 6 carbon atoms, typically from about 6 to 50 carbon atoms, preferably 6 to 15 carbon atoms, can be converted to isomers thereof by contacting the same with hydrogen in the presence of the catalyst system defined hereinafter. Mixtures of acyclic and alicyclic hydrocarbons can be used as the process feed stock. In a typical commercial operation, a paraffin stream containing mixtures of various types of open chain and closed chain paraffins is used as the process feed stock.

Hydrogen employed in the present isomerization process may be derived from any suitable source. Typically, in a refinery operation, the hydrogen employed may be a crude or an impure hydrogen stream such as that obtaine from a naphtha reforming operation. The hydrogen need not be purified for sulfur removal prior to the use as the present catalyst can tolerate substantially any amount of sulfurbearing materials, provided that the molar ratio of sulfur compounds to metal halide does not substantially exceed about 1:1. Alternatively, hydrogen may be generated in situ by introducing hydrogen donors into the reaction zone during the course of the reaction. Examples of useful hydrogen donors include materials such as decalin, tetralin, methylcycloheaxane and the like. Most preferably, elemental hydrogen is introduced into the reaction zone.

The hydroisomerization reaction may be carried out in bulk, that is, in the absence of any solvent or in the presence of a solvent or diluent material. Useful solvent or diluent compositions include fluorinated paraffins, sulfolane, sulfur dioxide, sulfurylchloride fluoride, fluorinated acids and/or acid anhydrides, hydrogen fluoride and the like. Hydrogen fluoride is the preferred reaction diluent when the metal halide portion of the catalyst system is a metal fluoride. When hydrogen fluoride is the diluent with catalysts made up of metal chlorides or bromides, an exchange reaction results converting the metal halide material to the metal fluoride. When a solvent or diluent is used, sufficient amounts are employed to maintain the viscosity of the reaction mixture at a desired level. Typically, from about 0.25 to 50, preferably from about 1 to 20 volumes of solvent of diluent are used per volume of hydrocarbon feed stock.

The catalyst system used in the present hydroisomerization process is composed of a difficulty reducible metal halide in combination with a hydrogen halide. Useful metal halide constituents include the flurorides, bromides and chlorides and niobium, tantalum, molybdenum and tungsten and the chlorides and bromides of aluminum and gallium. The preferred metal halide catalyst constitutents are tantalum and niobium halides, preferably tantalum pentafuoride, niobium pentafluoride and mixtures thereof.

The second component of the catalyst system is a hydrogen halide. Useful materials include hydrogen bromide, hydrogen chloride, and hydrogen fluoride. It is desirable in order to avoid exchange reactions, that the halide moiety of the hydrogen halide be one that will not cause disadvantageous exchange reactions with the metal halide constituent of the catalyst system. For example, if tantalum pentabromide is used as the metal constituent, the preferred hydrogen halide co-catalyst would be hydrogen bromide since the halogen moieties of both hydrogen chloride and hydrogen fluoride would exchange with the bromine atoms of the tantalum bromide metal constituent. Desirably, the halide moiety of the hydrogen halide and the metal halide are the same. The preferred hydrogen halide catalyst constituent is hydrogen fluoride.

Catalyst effectiveness is related to the molar ratio of hydrogen halide to metal halide catalyst constitutents. At least an equal molar amount of hydrogen halide relative to metal halide should be present in the reaction zone. Desirably, the hydrogen halide/metal halide ratio is at least 2:1, preferably at least about 5:1. In the case of catalyst systems based on tantalum pentafluoride and niobium pentafluoride, the presence of large (5:1 to about 20:1) molar excesses of hydrogen fluoride in the reaction zone has been found to materially improve reaction rates in the presence of poisons. Depending upon the relative amounts of catalyst constituents used, the catalyst may be a homogeneous solution of hydrogen halide and metal halide or a mixture of solid and dissolved metal halide in hydrogen halide.

Except when feed stocks containing sulfur compounds are used, the amount of metal halide catalyst component present in the reaction zone is not critical. Typically, from about 0.001 to 10, preferably 0.01 to 5.0 weight parts of metal halide are present in the reaction zone per weight part of hydrogen reactant. When sulfur compound impurities are present in the feed stock, it is desirable, if maximum catalyst activity is desired, to have a molar excess of metal halide present in the reaction zone relative to the amount of sulfur poison present in the reaction zone at any point in time. Sulfur compounds are believed to form complexes with the catalyst constituents. It is believed that an equilibium is established between the amount of sulfur complex formed and the amount of sulfur in the hydrocarbon phase. Accordingly, not all of the sulfur present reacts with or complexes with the catalyst constituents. Further, the complex forming reactions appear to be reversible via an equilibrium reaction or a cleavage reaction in that the concentration of sulfur in the acid layer can be diminished when the catalyst is contacted with a sulfur-free feed stock.

While the present system is not adversely affected by the presence of benzene or other aromatic compounds, sulfur compounds or unsaturated organic compounds (e.g. olefinic materials), the feed stocks, diluents, and individual catalyst constituents should be purified prior to use to remove water if maximum catalyst activity is desired. The presence of small amounts of water is tolerable if the corresponding catalyst loss or drop in catalyst activity is desired or can be accepted. Preferably, the amount of water within the reaction zone should not exceed about 0.01 wt. %, preferably about 1 wppm, based on total feed.

In one embodiment of the present invention, the reaction zone comprises a single reactor with a single temperature zone wherein the hydroisomerization is effected at said temperature, the reaction zone being maintained at said temperature by using the hydrogen halide component of the catalyst as an autorefrigerant. In another embodiment of the present invention, the reaction zone may comprise a single reactor having at least two temperature zones, the high temperature zone existing prior to the existence of the lower temperature zone. In a further embodiment of the present invention, the reaction zone may comprise a plurality of serially connected reactors, the temperature of the first reactor being at least that of one subsequent reactor. Thus, the reaction zone may comprise a single temperature zone or a high temperature zone followed by a lower temperature zone, each reaction zone i.e. contains at least one temperature zone. In still another embodiment of the present invention, the reaction zone may comprise several reactors in series with a temperature gradient between each reactor. Other configurations obvious to one or ordinary skill in the art are contemplated.

In general, hydroisomerization reaction temperatures of the present invention will vary from about 0° C to about the critical temperature of the acid formed from the hydrogen halide. When the hydrogen halide is hydrogen fluoride, the temperature will preferably be in the range of from about 0° to about 150°, most preferably from about 25° to about 100° C. If the reaction zone comprises a single reactor and hydrogen fluoride is employed, the temperature will preferably be maintained in the range of from about 40° to about 80° C. If the reaction zone contains two reactors and hydrogen fluoride is employed, each reactor corresponding to a different temperature zone, the temperature of the higher temperature zone will range from about 40° to about 100° C, preferably from about 50° to about 90° C. The temperature of the lower temperature zone will range from about 0° to about 60° C, preferably from about 20° to about 50° C. The temperature of the reaction zone is important during autorefrigeration because, at a given pressure, the higher the temperature, the more hydrogen halide removed with the hydrogen and hydrocarbon vapor, i.e. the more heat of reaction removed by autorefrigeration. In addition, the higher the temperature, the higher the reaction rate. However, the equilibrium established during hydroisomerization at higher temperatures is less favorable to the formation of desirable large amounts of higher octane constituents than at lower temperatures. Therefore, rather than employing a single temperature reaction zone and having to compromise between reaction rate, along with heat removal via autorefrigeration, and equilibrium when choosing the optimum temperature, a two temperature reaction zone system may be employed. Such a system may be obtained in a single reactor with two temperature zones or in two reactors in series, each reactor at a different temperature. In the latter case, a poorer equilibrium is reached rapidly in the high temperature first stage, wherein the high heat of reaction (including that due to benzene and feed olefin hydrogenation) is easily removed by the high hydrogen halide boil-off, while the lower temperature second stage allows for obtaining an improved equilibrium with reasonable residence time and little autorefrigeration duty due to the relatively small additional heat of reaction occurring therein. The principal cooling duty in the lower temperature stage is that required to cool the hydrocarbons passing to that stage from the higher temperature stage.

The isomerization reaction is preferably conducted at a total pressure sufficient to maintain the hydrocarbon feed stock and catalyst in substantially the liquid phase. Hydrogen partial pressures in the reaction zone may vary widely, but should be sufficient to maintain acceptable catalyst activity. Typically, the hydrogen partial pressure should be at least about 5 psig, preferably from about 5 to about 2,000 psig, more preferably from about 25 to about 2,000 psig, and still more preferably from about 25 to about 400 psig. The amount of hydrogen relative to the amount of hydrocarbon feed stock depends upon temperature, hydrogen partial pressure and autorefrigeration duty. Typically, however, from about 0.05 to 2.5 moles, preferably from about 0.05 to about 1 mole, of hydrogen per mole of hydrocarbon feed stock are contacted in the reaction zone.

In general, the reaction time varies from about 0.5 to about 1,500 minutes, preferably from about 1 to about 500 minutes. In the embodiment employing two reactors, the elevated temperature in the higher temperature zone increases the rate of reaction which in turn reduces the total reaction time required to accomplish the desired level of isomerization. Thus, since reaction time is related to reaction temperature and hydrogen partial pressure, the reaction time of the higher temperature zone-low temperature zone two-reactor system will be no greater than that of the single temperature zone-single reactor embodiment operating to the same isomerization yield. In general, the process is conducted for a time sufficient to secure a product from the lower temperature zone enriched in an isomer of at least one of the hydrocarbon components from the higher temperature zone.

The hydrocarbon product leaving the reaction zone will contain both dissolved and entrained catalyst, in particular from about 5 to about 10,000 wppm of metal halide, which should be removed therefrom to avoid undesirable product contamination with non-hydrocarbon materials. In addition, the removal of metal halide from the hydrocarbon product stream would be beneficial to prevent the risk of process equipment fouling and corrosion due to its presence. Further, returning the recovered metal halide to the reaction zone would represent a cost savings. One method for obtaining such recovery is described in U.S. Pat. No. 3,830,871 wherein the metal halide is removed from hydrocarbons by contacting same with substantially anhydrous (i.e. containing less than 2 wt. % water) liquid hydrogen halide solvent in a hydrogen halide to hydrocarbon volume ratio ranging from about 1:100 to about 1:1, perferably from about 1:50 to 1:5. Contact of the hydrogen halide solvent with the hydrocarbon stream preferentially extracts the metal halide into the solvent, i.e., the solublity of metal halide in the hydrogen halide is much higher than in the hydrocabon product such that the metal halide is recovered substantially quantitatively. The contacting is typically effected at a temperature ranging from about the freezing point to the critical temperature of the hydrogen halide and at a pressure in the range of the isomerization pressures mentioned above. The contacting is preferably carried out in a counter-current liquid-liquid extraction column. According to the patent, the resultant extract is then distilled such that the hydrogen halide taken overhead is condensed and then recycled to the contacting zone as fresh extraction solvent. The bottoms from the distillation, a concentrated solution of metal halide in hydrogen halide, is settled to remove any insoluble hydrocarbons present therein and then recycled to the reaction zone and combined with the catalyst phase.

However, in using the present invention, the distillation of the extract and associated steps may be eliminated by simply recycling the extract directly to the reaction zone wherein the hydrogen halide is used as the autorefrigerant and will be removed overhead as vapor from the system. Thus, the reaction zone overhead condensate, which comprises hydrogen halide substantially free of metal halide, can now again be used entirely or in part as extraction solvent for catalyst recovery. However, in this method, the amount of hydrogen halide available for the extraction is established by the reaction zone heat balance in that the more heat of reaction to be removed by autorefrigeration, the more hydrogen halide will be available for this purpose. Normally, the amount available will exceed the requirements, but if this is not the case, a simple preheat of the feed to the reaction zone or some heating of the reaction zone will rectify any discrepancy. Elimination of the extract distillation not only eliminates several pieces of equipment, e.g. distillation column, reboiler and overhead condenser, but also reduces utility requirements, e.g. heating and cooling duties. In addition, any catalyst deactivation or hydrocarbon product degradation that might occur in the bottom of the distillation tower is avoided.

Other advantages of the present invention will be more clearly understood by the description below and by reference to the accompanying Figure. Such details are included as are necessary for a clear understanding of how the present invention operates. No intention is made to unduly limit the scope of the present invention to the particular configuration shown as other configurations are contemplated. Various items such as valves, pumps, compressors, steam lines, instrumentation, and other process equipment and control means have been omitted therefrom for the sake of simplicity. Variations obvious to those having ordinary skill in the art of isomerization processes are included within the broad scope of the present invention.

Referring now to the Figure, the system illustration shows a two-reactor, two-temperature zone isomerization process comprising a high temperature autorefrigerated isomerization reactor 1 and a low temperature autorefrigerated isomerization reactor 2. A feed stock containing isomerizable hydrocarbons is introduced into reactor 1 via line 3 and contacted, in the presence of hydrogen, with preferred isomerization catalyst comprising tantalum pentafluoride in combination with at least a molar equivalent of hydrogen fluoride. If desired, the hydrocarbon feed stock may also be suitably pretreated for the removal of contaminants, e.g., water, sulfur compounds and the like, prior to entering reactor 1. In this particular embodiment, the hydrogen is introduced into reactor 2 via line 4 and passes therethrough entering reactor 1 via line 5. Alternatively, the hydrogen can be introduced directly into reactor 1, alone or in combination with that contained in line 5. Reactor 1 is maintained at a relatively high temperature, preferably within the range of from about 40° to about 100° C., so as to accelerate the rate of reaction several fold (typically, the reaction rate doubles for every 10° C increase in temperature). The higher temperature permits the use of a smaller reactor and less catalyst inventory than possible at lower temperatures.

The temperature is maintained within said range by allowing the hydrogen fluoride, together with some of the lighter hydrocarbons, to boil off so as to remove the heat evolved during the isomerization reaction. The resulting vapors which comprise hydrogen fluoride, hydrogen, and hydrocarbon are then passed from reactor 1 via line 6 through condenser 7 and via line 8, into separator 9. In separator 9, the overhead products from reactor 1 are separated into a gas stream comprising hydrogen fluoride, uncondensed light hydrocarbons, and hydrogen, a hydrocarbon liquid stream, and a liquid stream comprising substantially hydrogen fluoride. The gas stream and hydrocarbon liquid stream leave separator 9 via lines 10 and 11, respectively. The liquid hydrogen fluoride stream leaves the separator 9 via line 12 and is combined with a corresponding stream from reactor 2 as will be described hereinbelow.

A stream comprising partially isomerized hydrocarbon feed stock is passed from reactor 1 into reactor 2 via line 13 and further isomerized in the presence of the catalyst and hydrogen, the latter being introduced via line 4 as mentioned above. Reactor 2 is operated at a lower temperature level than reactor 1 to shift the thermodynamic equilibrium toward higher yields of branched paraffinic isomers. The temperature of reactor 2 will preferably range from about 0° to about 60° C, but lower than that of reactor 1. The lower temperature of reactor 2 maay be achieved and maintained by allowing the hydrogen fluoride to boil off, i.e., autorefrigeration in reactor 2. As in the higher temperature reactor 1, the vapors arising from autorefrigeration pass via line 14 into condenser 15 and then via line 16 into separator 17. A gaseous stream comprising hydrogen fluoride, uncondensed light hydrocarbons, and hydrogen passes from separator 17 through line 5 into reactor 1. A hydrocarbon liquid stream is withdrawn through line 18, while a liquid stream 19 comprising hydrogen fluoride is combined with corresponding stream 12 from separator 9 to form stream 20 which comprises substantially liquid hydrogen fluoride. Alternatively, if desired, the autorefrigeration vapor leaving reactor 2 via line 14 may be passed directly into reactor 1, thus eliminating the need for condenser 15 and separator 17. When done in this manner, the vapor entering reactor 1 will be richer in the hydrogen fluoride and uncondensed hydrocarbon than the vapor from separator 17. Since, for a given temperature and pressure, the amount of hydrogen fluoride and hydrocarbon in a given amount of hydrogen leaving reactor 1 is fixed, less autorefrigeration can be done by a vapor which has not been subjected to intermediate condensation, i.e., the vapor is not as lean in hydrogen fluoride and thus cannot remove as much heat. However, depending on the temperature differential between reactors 1 and 2, sufficient autorefrigeration capacity may exist to permit elimination of the costly condensation equipment in line 14. When this alternative method is employed such that condenser 15 and separator 17 are eliminated, it may be desirable to combine reactors 1 and 2 into a single reactor.

Isomerized hydrocarbon product containing small amounts of dissolved and entrained catalyst is removed from reactor 2 via line 21 and introduced, along with stream 20, into contacting tower 22, wherein tantalum pentafluoride may be removed from the hydrocarbon product by liquid-liquid extraction with hydrogen fluoride solvent according to the method described in U.S. Pat. No. 3,830,871, the disclosures of which are incorporated herein by reference. As shown in the Figure, an extract phase comprising hydrogen fluoride, some hydrocarbon material and the tantalum pentafluoride removed from the hydrocarbon product is withdrawn from the contacting tower via line 24 and recycled to reactors 1 and 2 via lines 25 and 26, respectively. A raffinate phase comprising isomerized hydrocarbon product having a reduced tantalum pentafluoride content and containing soluble amounts of hydrogen fluoride is discharged from the contacting tower 22 via line 23.

If desired, hydrogen fluoride may be recovered from the hydrocarbon product by distillation to yield a substantially hydrogen fluoride-free hydrocarbon product. Alternatively, hydrogen fluoride may be removed from the hydrocarbon product by contacting same with hydrogen gas. This may be done in a suitable contacting zone, e.g. a vapor-liquid stripping zone, such that there results a liquid phase comprising substantially hydrogen fluoride-free hydrocarbon and a gaseous phase comprising hydrogen and hydrogen fluoride. If desired, the gaseous phase may be used as the source of hydrogen in line 4 and/or 5 of the Figure. This method of removing fluoride from the isomerized hydrocarbon product has the advantage of using a hydrogen fluoride-free gas stream, which will become saturated with hydrogen fluoride upon passage through the contacting zone, to remove the hydrogen fluoride dissolved in said product prior to introduction of the gas into the reaction zone. The hydrogen is thus a gratuitously available stripping gas stream, the use of which obviates the necessity of supplying an extraneous hydrogen fluoride-free dry stripping gas, e.g. propane, the need for hydrogen fluoride removal from the used extraneous stripping gas and the possible need for a recycle gas compressor. This method for removing hydrogen fluoride has a further advantage in that if the make-up hydrogen entering via line 4 contains traces of hydrocarbon soluble contaminants, e.g. $H_2O$, $CO_2$, $H_2S$, and the like, contact with the hydrogen fluoride will effectively remove such potential contaminants from the hydrogen prior to its introduction into the reaction zone.

Reactions involving the use of metal fluoride/hydrogen fluoride catalyst systems can be conducted in vessels fabricated from carbon steel provided that excessive temperatures are not used and provided further that the reaction system is maintained in a substantially anhydrous condition. However, at temperatures above about 65° C, alloy materials such as monel, aluminum 5052 and the like, as well as Teflon, may be required.

By using the two reactor, two-temperature zone system described above, the reaction time required to produce the same amount of isomerate as that produced by the conventional, lower temperature operation is reduced. Thus, more isomerate can be made in less time by this embodiment of this invention than by a single operation at lower temperatures. In addition, the temperature of each temperature zone may be controlled by autorefrigeration, i.e., allowing the hydrogen halide to boil off. This method of removing heat evolved from the isomerization reaction is much more efficient than by the indirect heat transfer techniques employed in the prior art. Pumparounds and expensive coolers are not required to control the temperature of the reaction zone. For a given conversion, i.e. heat of reaction, the amount of hydrogen halide boil-off is determined by the latent heat of the hydrogen halide and the co-boiling hydrocarbon and the desired temperature for conducting the isomerization.

However, if the conversion achieved in reactor 1 is sufficient to obtain the desired octane improvement, reactor 2 and its associated equipment can be eliminated such that the isomerization is carried out in a single autorefrigerated reaction zone which is maintained at one temperature. In such case, the hydrogen fluoride condensed from the overhead vapors will be used in contacting tower 22, such that the extract may be returned to reactor 1 via lines 24, 25. While the embodiment shown in the Figure describes two reactors, it should be understood that three or more reactors can also be utilized.

The following examples are presented to further illustrate the process of the present invention and are not intended to unduly restrict the limits of the claims appended hereto. Unless otherwise specified, all percentages and parts are by weight.

EXAMPLE 1

Into a one liter Parr Model 4,521 stirred Hastelloy C reactor in a dry box was placed tantalum pentafluoride (138.0 g, 0.50 mole). The reactor was removed from the dry box, sealed, and partially evacuated. Hydrogen fluoride (83.0 g, 4.2 mole) was added from a pressurized cylinder through a gas sampling valve by direct connection. A hydrocarbon feed (220 ml, ~1.8 mole) comprising n-pentane (34 vol.%), 3-methylpentane (28 vol. %) n-hexane (22vol. %), cyclohexane (11 vol. %) and benzene (5 vol. %) was then introduced from a precharged cylinder pressurized with hydrogen. The stirrer was turned on at 1000 rpm and the reactor pressure was adjusted to 50 psi of hydrogen partial pressure (42 pounds of hydrogen partial pressure equals about 0.1 mole). The reactor mixture was then heated rapidly (~ 2 minutes) to 71° C by passing steam through coils internal to the reactor. When conditions of 71° C and 150 psig total pressure were reached, a liquid hydrocarbon sample was taken, with samples being taken at varying intervals thereafter, by connecting an evacuated 10 milliliter stainless steel high pressure cylinder to the 1 liter reactor. The line connecting the reactor and cylinder (~2 ml in volume) was used as a lock-hopper. As such, it was equipped with vacuum to facilitate product removal into the 10 ml cylinder and hydrogen to blow back product trapped in the sampling dip leg. The reactor valve was opened to permit 2 ml of sample to be trapped in the lockhopper. The 10 ml cylinder valve was then opened to transfer the hydrocarbon sample. The sample cylinder was cooled to $-70°$ C and 0.1 $\mu$l aliquots were analyzed on an Aerograph Model 1520 Gas Chromatograph with a 15 ft $\times$ ⅛ inch 15% squalane on 80/100 Chromosorb P at 90° C. The analysis showed the distribution of products and conversions given below:

| Sample No. | 1 | 2 | 3 | 4 | 5 |
|---|---|---|---|---|---|
| Temperature, ° C. | | | 71 | | |
| Sample Time, Min. | 0 | 2 | 5 | 7 | 10 |
| Analysis of Hydrocarbon Liquid, wt. % | | | | | |
| (C$_3$) | (1) | (1) | (1) | (1) | (1) |
| i-C$_4$ | 0.05 | 0.41 | 1.32 | 1.94 | 2.38 |
| n-C$_4$ | 0.04 | 0.16 | 0.32 | 0.43 | 0.48 |
| i-C$_5$' | 7.00 | 25.56 | 27.38 | 26.88 | 26.81 |
| n-C$_5$ | 26.43 | 8.06 | 6.10 | 6.34 | 5.86 |
| 2,2-DMC$_4$ | 2.30 | 17.18 | 24.09 | 24.67 | 25.77 |
| 2,3-DMC$_4$ and 2-MC$_5$ | 22.25 | 23.08 | 21.02 | 20.86 | 21.30 |
| 3-MC$_5$ | 8.10 | 7.62 | 7.00 | 7.34 | 6.90 |
| n-C$_6$ | 19.47 | 6.40 | 4.23 | 4.27 | 4.12 |
| MCP | 1.37 | 1.45 | 1.16 | 1.21 | 0.80 |
| C$_6$H$_6$ | 3.88 | 2.66 | 1.70 | 1.30 | 0.96 |
| CyC$_6$ | 9.12 | 7.41 | 5.68 | 4.75 | 4.61 |
| Total | 100.01 | 99.99 | 100.00 | 99.99 | 99.99 |
| Conversions | | | | | |
| C$_4$- | 0.09 | 0.57 | 1.64 | 2.37 | 2.86 |
| i-C$_5$'s | 33.43 | 33.62 | 33.48 | 33.22 | 32.67 |
| wt. % 2,2-DMC$_4$ in C$_6$H$_{14}$'s | 4.40 | 31.65 | 42.76 | 43.17 | 44.36 |
| n-C$_6$, % Conv. | — | 67.13 | 78.27 | 78.07 | 78.84 |
| CyC$_6$, % Conv. | — | 2.85 | 25.00 | 34.65 | 40.68 |
| C$_6$H$_6$, % Conv. | — | 31.44 | 56.19 | 66.49 | 75.26 |

(1) Not available due to equipment malfunction.

At the end of a ten minute cycle at 71° C. the reactor was cooled to 50° C. and 100 psig by passing cold water through the reactor's internal cooling coils for about 3 minutes to simulate autorefrigeration conditions, sampled, and allowed to equilibrate. The samples were taken periodically and analyzed as before to give the results shown below:

| Sample No. | 6 | 7 | 8 | 9 |
|---|---|---|---|---|
| Temperature, °C. | | | 50 | |
| Sample Time, min. | 0 | 10 | 20 | 30 |
| Analysis of Hydrocarbon | | | | |
| Liquid, wt. % | | | | |
| $C_3$ | 0.54 | 0.59 | 0.59 | 0.42 |
| i-$C_4$ | 2.61 | 2.84 | 2.83 | 2.33 |
| n-$C_4$ | 0.48 | 0.60 | 0.60 | 0.54 |
| -$C_5$ | 27.06 | 27.51 | 27.08 | 25.64 |
| n-$C_5$ | 5.64 | 5.27 | 5.86 | 5.24 |
| 2,2-$DMC_4$ | 26.31 | 27.63 | 28.10 | 29.19 |
| 2,3-$DMC_4$ and 2-$MC_5$ | 20.74 | 19.60 | 19.75 | 20.93 |
| 3-$MC_5$ | 6.63 | 6.56 | 6.31 | 6.68 |
| n-$C_6$ | 3.91 | 3.50 | 3.47 | 3.74 |
| MCP | 0.65 | 0.71 | 0.62 | 0.57 |
| $C_6H_6$ | 0.88 | 0.68 | 0.72 | 0.73 |
| $CyH_6$ | 4.54 | 4.12 | 4.08 | 3.99 |
| Total | 99.99 | 99.99 | 99.99 | 99.99 |
| Conversions | | | | |
| $C_4$- | 3.63 | 4.03 | 4.02 | 3.29 |
| i-$C_5$'s | 32.70 | 32.78 | 32.94 | 30.88 |
| wt. % 2,2-$DMC_4$ in $C_6H_{14}$'s | 45.69 | 48.23 | 48.76 | 48.22 |
| n-$C_6$, % Conv. | 79.92 | 82.02 | 82.18 | 80.79 |
| $CyC_6$, % Conv. | 50.52 | 53.96 | 55.20 | 56.53 |
| $C_6H_6$, % Conv. | 77.32 | 82.47 | 81.44 | 81.19 |

The first analysis shows that at 71°C., isomerization thermodynamic equilibrum can be reached in about 10 minutes. At that point, the isohexane product contains about 44 wt. % of 2,2-$DMC_4$ (MON of 2,2-$DMC_4$ is 93.4). The second set of data shows that when the boiling-off of hydrogen fluoride under hydrogen partial pressure is simulated by reducing the temperature to 50° C., the reaction product reaches a new thermodynamic equilibrium in about 10 minutes wherein the amount of the high MON 2,2-$DMC_4$ component in the isohexane product has increased to over 48 wt. %

EXAMPLE 2

The two part experiment in Example 1 was repeated with the same catalyst and a fresh sample of feed stock to show that the catalyst was not deactivated over the temperatures employed.

At the end of a cycle the reactor was placed in an ice-water bath an at ~10° C., the hydrocarbon product was removed (~80%) through the sampling dip leg and the pressure was slowly vented to 25 psig. While still at ~10° C. a charge of fresh feed was added, the reactor agitated a few times and the feed removed as above. This step was employed to maintain initial low conversion levels, since only ~80% of the hydrocarbon volume could be removed. The fresh feed for the new cycle was then added, the reactor reinstalled, and the reaction was repeated as above over the same catalyst. The results are shown below:

| Sample No. | 1 | 2 | 3 | 4 | 5 |
|---|---|---|---|---|---|
| Temperature, °C. | | | 71 | | |
| Sample Time, Min. | 0 | 2 | 5 | 7 | 10 |
| Analysis of Hydrocarbon | | | | | |
| Liquid, wt. % | | | | | |
| $C_3$ | 0.06 | 0.07 | 0.13 | 0.21 | 0.24 |
| i-$C_4$ | 0.29 | 0.40 | 0.88 | 1.37 | 1.91 |
| n-$C_4$ | 0.30 | 0.08 | 0.15 | 0.22 | 0.29 |
| i-$C_5$ | 6.78 | 19.51 | 22.79 | 23.14 | 22.97 |
| n-$C_5$ | 18.50 | 8.71 | 5.45 | 5.20 | 5.27 |
| 2,2-$DMC_4$ | 3.33 | 13.26 | 21.79 | 24.71 | 25.35 |
| 2,3-$DMC_4$ and 2-$MC_5$ | 18.82 | 25.06 | 23.16 | 21.99 | 21.84 |
| 3-$MC_5$ | 6.95 | 8.42 | 7.65 | 7.21 | 7.26 |
| n-$C_6$ | 30.33 | 10.32 | 5.16 | 4.44 | 4.51 |
| MCP | 1.66 | 2.08 | 1.75 | 1.47 | 1.53 |
| $C_6H_6$ | 4.04 | 3.74 | 3.25 | 2.75 | 2.38 |
| $CyC_6$ | 8.94 | 8.34 | 7.82 | 7.29 | 6.45 |
| Total | 99.99 | 99.99 | 99.99 | 99.99 | 99.99 |
| Conversions | | | | | |
| $C_4$- | 0.65 | 0.56 | 1.16 | 1.80 | 2.44 |
| i-$C_5$'s | 25.28 | 28.22 | 28.24 | 28.34 | 28.44 |
| wt. % 2,2-$DMC_4$ in $C_6H_{14}$'s | 5.60 | 23.24 | 37.73 | 42.35 | 43.00 |
| n-$C_6$, % Conv. | — | 65.97 | 82.99 | 85.36 | 85.13 |
| $CyC_6$, % Conv. | — | 1.70 | 9.72 | 17.36 | 24.72 |
| $C_6C_6$, % Conv. | — | 7.43 | 19.55 | 31.93 | 41.09 |

| Sample No. | 6 | 7 | 8 | 9 |
|---|---|---|---|---|
| Temperature, °C. | | | 50 | |
| Sample Time, Min. | 0 | 10 | 20 | 30 |
| Analysis of Hydrocarbon | | | | |
| Liquid, wt. % | | | | |
| $C_3$ | 0.32 | 0.35 | 0.29 | 0.39 |
| i-$C_4$ | 2.66 | 2.71 | 2.77 | 2.97 |
| n-$C_4$ | 0.36 | 0.45 | 0.35 | 0.41 |
| i-$C_5$ | 23.49 | 23.68 | 23.66 | 23.99 |
| n-$C_5$ | 5.11 | 5.04 | 4.76 | 4.68 |
| 2,2-$DMC_4$ | 26.00 | 27.28 | 28.23 | 28.55 |
| 2,3-$DMC_4$ and 2-$MC_5$ | 21.53 | 20.77 | 20.48 | 20.36 |
| 3-$MC_5$ | 7.02 | 6.84 | 6.90 | 6.60 |
| n-$C_6$ | 4.25 | 3.84 | 3.73 | 3.66 |
| MCP | 1.19 | 1.17 | 1.14 | 1.06 |
| $C_6H_6$ | 1.93 | 1.73 | 1.65 | 1.62 |
| $CyH_6$ | 6.15 | 6.15 | 6.05 | 5.71 |
| Total | 99.99 | 99.99 | 99.99 | 99.99 |
| Conversions | | | | |
| $C_4$- | 3.34 | 3.51 | 3.41 | 3.77 |
| i-$C_5$'s | 28.60 | 28.72 | 28.42 | 28.67 |
| wt.% 2,2-$DMC_4$ in $C_6H_{14}$'s | 44.22 | 46.45 | 47.57 | 48.25 |
| n-$C_6$, % Conv. | 85.99 | 87.34 | 87.70 | 87.93 |
| $CyC_6$, % Conv. | 30.75 | 30.94 | 32.17 | 36.13 |
| $C_6H_6$, % Conv. | 52.22 | 57.18 | 59.16 | 59.90 |

This example shows that in the high temperature zone (71° Cl), the amount of 2,2-dimethylbutane in the hexane product increases rapidly from about 6 to about 43 wt. %. By simple autorefrigerating to 50° C. and stirring for about 10 minutes, a new equilibrium is approached wherein the 2,2-$DMC_4$ concentration increases to about 48 wt. % of the hexane product. Simultaneously, the concentration of the lower octane hexane isomers decreases in concentration such that an isomerate of enhanced octane is produced.

What is claimed is:

1. In an isomerization process which comprises reacting a hydrocarbon feed stock which comprises a saturated acyclic hydrocarbon having at least four carbon atoms, a saturated alicyclic hydrocarbon having at least six carbon atoms or mixtures thereof with hydrogen in a reaction zone comprising at least one reactor having therein at least one temperature zone and with a catalyst comprising a metal halide selected from the group consisting of the bromides and the chlorides of aluminum and gallium and the chlorides, bromides and fluorides of niobium, tantalum, molybdenum or tungsten and including in said isomerization zone at least an equal molar amount, based on the metal halide, of a hydrogen halide selected from the group consisting of hydrogen fluoride, hydrogen chloride and hydrogen bromide, at least a portion of said metal halide being dissolved in said hydrogen halide, said reaction zone being maintained at isomerization conditions which include at least a portion of the catalyst and hydrocarbon feed stock being in the liquid phase, thereby forming a reaction product of enhanced octane, the improvement which comprises controlling the temperature in said at least one temperature zone by vaporizing at least a portion of said hydrogen halide.

2. The process of claim 1 wherein said reaction product contains from about 5 to about 10,000 wppm of said metal halide, and wherein at least a portion of the vaporized hydrogen halide autorefrigerant is condensed and then contacted with said reaction product to from a raffinate having a reduced content of said metal halide and an extract comprising said liquid hydrogen halide enriched in said metal halide, at least a portion of said extract being recycled to the reaction zone.

3. The process of claim 1 wherein the molar ratio of hydrogen halide to metal halide present in said reaction zone is at least 2:1.

4. The process of claim 1 wherein said isomerization is conducted at a temperature in the range of from about 0° C to about the critical temperature of the hydrogen halide.

5. The process of claim 1 wherein the metal halide is a metal fluoride and the hydrogen halide is hydrogen fluoride.

6. The process of claim 5 wherein the metal fluoride is tantalum pentafluoride, niobium pentafluoride or mixtures thereof.

7. The process of claim 6 wherein the molar ratio of hydrogen fluoride to metal fluoride present in the reaction zone is at least 2:1.

8. The process of claim 7 wherein the hydrogen partial pressure is at least 5 psig.

9. In an isomerization process which comprises reacting a hydrocarbon feed stock which comprises a saturated acyclic hydrocarbon having at least 4 carbon atoms, a saturated alicyclic hydrocarbon having at least 6 carbon atoms or mixtures thereof, with hydrogen in a reaction zone comprising at least one reactor having therein at least one temperature zone and with a catalyst comprising tantalum pentafluoride, niobium pentafluoride or mixtures thereof and hydrogen fluoride, the molar ratio of hydrogen fluoride to metal fluoride present in the reaction zone being at least 2:1, at least a portion of said metal fluoride being dissolved in said hydrogen fluoride, said reaction zone being maintained at substantially liquid phase catalyst isomerization conditions including a temperature ranging from about 0° C. to the critical temperature of the hydrogen fluoride, and a hydrogen partial pressure varying from about 5 to about 2000 psig, thereby forming a reaction product of enhanced octane, the improvement which comprises controlling the temperature in said at least, one temperature zone by vaporizing at least a portion of said hydrogen fluoride.

10. The process of claim 9 wherein the feed stock comprises a saturated acyclic hydrocarbon having from 4 to 10 carbon atoms, a saturated alicyclic hydrocarbon having from 6 to 15 carbon atoms or mixtures thereof.

11. The process of claim 9 wherein said reaction product contains from about 5 to about 10,000 wppm of metal fluoride, and wherein at least a portion of the vaporized hydrogen fluoride autorefrigerant is condensed and then contacted with said reaction product to form a raffinate having a reduced content of said metal fluoride and an extract comprising said liquid hydrogen fluoride enriched in said metal fluoride, at least a portion of said extract being recycled to the reaction zone.

12. The process of claim 9 wherein said isomerization is conducted at a temperature in the range of from about 0° to about 150° C.

13. The process of claim 9 wherein the molar ratio of hydrogen fluoride to metal fluoride present in the reaction zone is at least about 5:1.

14. In an isomerization process which comprises reacting a hydrocarbon feed stock which comprises a saturated acyclic hydrocarbon having at least four carbon atoms, a saturated alicyclic hydrocarbon having at least 6 carbon atoms and mixtures thereof, with hydrogen in a reaction zone comprising at least one reactor having therein at least two temperature zones, the isomerization temperature of the first temperature zone being greater than the isomerization temperature of the second temperature zone, and with a catalyst comprising a metal halide selected from the group consisting of the bromides and chlorides of aluminum and gallium and the chlorides, bromides and flourides of niobium, tantalum, molybdenum or tungsten and at least an equal molar amount, based on the metal halide, of a hydrogen halide selected from the group consisting of hydrogen fluoride, hydrogen chloride and hydrogen bromide, at least a portion of said metal halide being dissolved in said hydrogen halide, said reaction zone being maintained at isomerization conditions which include at least a portion of the catalyst and the hydrocarbon feed stock being in the liquid phase, the improvement which comprises forming an isomerate of enhanced octane by controlling the temperature in at least one of said temperature zones by vaporizing a portion of said hydrogen halide.

15. The process of claim 14 said reaction product contains from about 5 to about 10,000 wppm of said metal halide, and wherein at least a portion of the vaporized hydrogen halide autorefrigerant is condensed and then contacted with said reaction product to form a raffinate having a reduced content of said metal halide and an extract comprising said liquid hydrogen halide enriched in said metal halide, at least a portion of said extract being recycled to the reaction zone.

16. The process of claim 14 wherein the molar ratio of hydrogen halide to metal halide present in said reaction zone is at least 2:1.

17. The process of claim 14 wherein said isomerization is conducted at a temperature in the range of from about 0° C. to about the critical temperature of the hydrogen halide.

18. The process of claim 14 wherein the metal halide is a metal fluoride and the hydrogen halide is hydrogen fluoride.

19. The process of claim 18 wherein the metal fluoride is tantalum pentafluoride, niobium pentafluoride or mixtures thereof.

20. The process of claim 19 wherein the molar ratio of hydrogen fluoride to metal fluoride present in the reaction zone is at least 2:1.

21. The process of claim 20 wherein the hydrogen partial pressure is at least 5 psig.

22. In an isomerization process which comprises reacting a hydrocarbon feed stock which comprises a saturated acyclic hydrocarbon having at least four carbon atoms, a saturated alicyclic hydrocarbon having at least six carbon atoms or mixtures thereof, with hydrogen in a reaction zone comprising at least one reactor having therein at least two temperature zones, the isomerization temperature of the first temperature zone being greater than the isomerization temperature of the second temperature zone, and with a catalyst comprising tantalum pentafluoride, niobium pentafluoride or mixtures thereof and hydrogen fluoride, the molar ratio of hydrogen fluoride to metal fluoride present in the reaction zone being at least 2:1, at least a portion of said metal fluoride being dissolved in said hydrogen fluoride, said reaction zone being maintained at substantially liquid phase catalyst isomerization conditions including a temperature ranging from about 0° C. to the critical temperature of the hydrogen fluoride and a hydrogen partial pressure varying from about 5 to about 2000 psig, the improvement which comprises forming an isomerate of enhanced octane by controlling the temperature in at least one of said temperature zones by vaporizing at least a portion of said hydrogen fluoride.

23. The process of claim 22 wherein the feed stock comprises a saturated acyclic hydrocarbon having from 4 to 10 carbon atoms, a saturated alicyclic hydrocarbon having from 6 to 15 carbon atoms or mixtures thereof.

24. The process of claim 22 wherein said reaction product contains from about 5 to about 10,000 wppm of metal halide, and wherein at least a portion of the vaporized hydrogen fluoride autorefrigerant is condensed and then contacted, in an extraction zone, with said reaction product, thereby forming a raffinate having a reduced content of said metal fluoride and an extract comprising said liquid hydrogen fluoride, at least a portion of said extract being recycled to the reaction zone.

25. The process of claim 22 wherein said isomerization is conducted at a temperature in the range of from about 0° to about 150° C.

26. The process of claim 22 wherein the molar ratio of hydrogen fluoride to metal fluoride present in the reaction zone is at least about 5:1.

* * * * *